United States Patent
Miyata et al.

(10) Patent No.: US 7,901,724 B2
(45) Date of Patent: Mar. 8, 2011

(54) FERMENTED TEA OBTAINED BY TEA-ROLLING PROCESSING OF TEA MATERIAL LEAVES AND LOQUAT LEAVES, AND COMPOSITION HAVING EXTRACT CONTAINED IN FERMENTED TEA AS ACTIVE COMPONENT

(75) Inventors: Yuuji Miyata, Isahaya (JP); Kiyonori Terai, Higashisonogi-gun (JP); Kei Tamaya, Omura (JP); Masamichi Maeda, Omura (JP); Seigou Hayashida, Omura (JP); Tomonori Tokushima, Isahaya (JP); Takashi Tanaka, Nishisonogi-kun (JP); Kazunari Tanaka, Nagasaki (JP); Shouko Nishizono, Miyazaki (JP); Toshiro Matsui, Fukuoka (JP)

(73) Assignees: Nagasaki Prefectural Government (JP); Nagasaki Prefectural and Municipal Universities Corporation (JP); Nagasaki University, National University Corporation (JP); Kyushu University, National University Corporation (JP)

( * ) Notice: Subject to any disclaimer, the term of this patent is extended or adjusted under 35 U.S.C. 154(b) by 949 days.

(21) Appl. No.: 11/670,360

(22) Filed: Feb. 1, 2007

(65) Prior Publication Data

US 2007/0190219 A1  Aug. 16, 2007

Related U.S. Application Data

(63) Continuation of application No. PCT/JP2005/014129, filed on Aug. 2, 2005.

(30) Foreign Application Priority Data

Aug. 3, 2004 (JP) .............................. P2004-227142
Jan. 7, 2005 (JP) .............................. P2005-002583

(51) Int. Cl.
*A23F 3/00* (2006.01)

(52) U.S. Cl. ......................... 426/597; 426/435

(58) Field of Classification Search .................. 426/435, 426/418, 385, 464, 465, 473, 599, 590, 597
See application file for complete search history.

(56) References Cited

U.S. PATENT DOCUMENTS

2003/0113406 A1 * 6/2003 Rao et al. .......................... 426/49

FOREIGN PATENT DOCUMENTS

| CN | 1086669 A | * | 11/1992 |
|---|---|---|---|
| CN | 1083315 A | * | 4/1993 |
| CN | 1093229 A | * | 4/1993 |
| CN | 1107312 A | | 8/1995 |
| CN | 1129525 A | * | 12/1995 |
| JP | 02-291229 | | 12/1990 |
| JP | 03-266954 | | 11/1991 |
| JP | 11169144 A | * | 6/1999 |
| JP | 2000-342229 | | 12/2000 |
| JP | 2001-069917 | | 3/2001 |
| JP | 2002-065227 | | 3/2002 |
| JP | 2002095415 A | * | 4/2002 |
| JP | 2003128571 A | | 5/2003 |
| JP | 2003-230358 | | 8/2003 |
| JP | 2003289834 A | | 10/2003 |
| JP | 2004105036 A | * | 4/2004 |
| JP | 2004141056 A | | 5/2004 |
| WO | 03014307 A2 | | 2/2003 |

OTHER PUBLICATIONS

Pintauro, Nicholas, Soluble Tea Prouduction Processes, 1970, Noyes Data Corporation, pp. 3-16.*

(Continued)

*Primary Examiner* — Jennifer C McNeil
*Assistant Examiner* — Hong Mehta
(74) *Attorney, Agent, or Firm* — St. Onge Steward Johnston & Reens LLP (57) ABSTRACT

A fermented tea produced by primary-drying tea material leaves by means of a primary tea rolling dryer (primary drying step) to adjust the moisture content of raw leaves (tea material leaves) of bancha with low qualities (the second crop of tea, the third crop of tea, the shuto-bancha, the skiffed leaves of tea, and the like) to a constant moisture; subsequently, providing them in a tea roller (tea rolling step); adding loquat leaves during the tea rolling step in order to knead loquat leaves together with the tea material leaves; and fermenting and drying the kneaded tea material leaves and loquat leaves. The fermented tea is formed into a composition having, as an active component, the fermented tea obtained by tea-rolling processing of tea material leaves and loquat leaves, and an extract contained in the fermented tea.

10 Claims, 6 Drawing Sheets

Linskens, H. F. and J.F. Jackson, Plant Volatile Analysis, 1997, vol. 19, Springer-Verlag Berlin Heidelberg, pp. 231-242.*

International Search Report; Oct. 26, 2005; 2 pages.

State Intellectual Property Office of People's Republic of China First Office Action & English translation: Application No. 200580026006.5; Issue Date: May 22, 2009; 10 pages.

Kazunari Tanaka, Yoko Nishizono, Yuki Miyata, Kei Tamaya, Masamichi Maeda, "Bancha Namacha to Kakinoha no Junen Kako ni yoru Hakkocha no Tonyobyo Yobo Koka", The Japanese Society of Nutritition and Food Science Sokai Koen Yoshishu, vol. 59th, Apr. 1, 2005; p. 144; English abstract included.

"Chemistry of Tea", edited Keiichiro Matsumura (Asakura Shoten) Mar. 15, 1991; pp. 124-191; English abstract included.

Mutsuo Kubo, Masayuki Takeuchi, "Chiiki Jibasanhin o Riyo shita Kenkocha Inryo no Kaihatsu", Reports of Kochi Prefectrual Industrial Technology Center, No. 28, 1986, pp. 26 to 29; English abstract included.

Kei Tamaya, Masamichi Maeda, Yuki Miyata, "Miriyo Shigen o Katsuyo shita Kokinosei Chaba no Kaihatsu", Nippon Shokuhin Kagaku Kogaku Taikai Koenshu, vol. 51st, Sep. 1, 2004; p. 47; English abstract included.

Japan Society for Bioscience, Biotechnology, and Agrochemistry, 2003, vol. 2003rd, p. 76, #2BOIa06 (Translation Provided).

Japan Society for Oriental Medicine, 2000, vol. 28, No. 2, pp. 61 to 63 (Translation Provided).

Japanese Office Action; Application No. JP 2006-531501; Jun. 15, 2010; 9 pages (translation provided).

Summary of Annual Meeting of the Pharmaceutical Society of Japan, 2003, vol. 123rd, No. 4, p. 165, #29 [P2]I-590 (translation provided).

* cited by examiner

FIG. 4
EGC REDUCTION RATIO

FIG. 5
EGCg REDUCTION RATIO

FIG. 6
COMPARISON OF TOTAL AMOUNT OF PRODUCED THEAFLAVINS

FIG. 7
COMPARISON OF AMOUNT OF PRODUCED THEASINENSINS

FERMENTED TEA OBTAINED BY TEA-ROLLING PROCESSING OF TEA MATERIAL LEAVES AND LOQUAT LEAVES, AND COMPOSITION HAVING EXTRACT CONTAINED IN FERMENTED TEA AS ACTIVE COMPONENT

CROSS-REFERENCE TO RELATED APPLICATIONS

The present application is a continuation of pending International patent application PCT/JP2005/014129 filed on Aug. 2, 2005 which designates the United States and claims priority from Japanese Patent Application No. 2004-227142 filed on Aug. 3, 2004 and Japanese Patent Application No. 2005-002583 filed on Jan. 7, 2005 the content of which is incorporated herein by reference.

FIELD OF THE INVENTION

The present invention relates to a composition having, as an active component, an extract contained in fermented tea obtained by means of tea-rolling processing of tea material leaves and loquat (*Eriobotrya japonica*) leaves in which unused resources of loquat leaves and tea material leaves are employed as raw materials. More particularly, since the aforementioned composition exhibits much more superior effects of controlling the elevation of blood glucose levels, compared to those of green tea or loquat tea known as being healthy, and exhibits effects of preventing diabetes, effects of obesity prevention, and effects of decreasing neutral fat levels in the serum and liver, the present invention relates to healthy foods, healthy beverages, and pharmaceutical compositions which are useful in treating and preventing lifestyle-related diseases.

BACKGROUND OF THE INVENTION

Heretofore, as a method for producing fermented tea, for example, a method for producing fermented tea or semi-fermented tea is known, in which fermented tea leaves or semi-fermented tea leaves are extracted with water at a temperature of less than 10° C. (the first step), an extraction residue in the first step is extracted with water heated to 50° C. (the second step), the extract obtained in the first step and the extract obtained in the second step are mixed, and subsequently, the mixture is subjected to a sterilization treatment (for example, see Patent Document 1) (referred to as Conventional Example 1).

In addition, a method for producing loquat tea is known, in which loquat leaves are not fermented alone, but loquat leaves are washed in a water tank for washing and removing floccuses, and at the same time, the floccuses on the rear surface of the loquat leaves are removed; subsequently, they are dried; semi-dried loquat leaves are sheared into small pieces; the sheared loquat leaves are subjected to solar drying; the solar-dried loquat leaves are mixed with tourmaline balls; and the mixture is roasted while mixing (for example, see Patent Document 2) (referred to as Conventional Example 2).

As the effects of green tea, antioxidation effects, anticancer effects, cancer prevention effects, effects of reducing cholesterol levels in the blood, effects of controlling the elevation of blood pressure, and the like are known (for example, see Non-patent Document 3) (referred to as Conventional Example 3).

[Patent Document 1]
Japanese Unexamined Patent Application, First Publication No. 2003-230358
[Patent Document 2]
Japanese Unexamined Patent Application, First Publication No. 2000-342229
[Non-patent Document 3]
"Chemistry of Tea", edited by Keiichiro MATSUMURA (Asakura Shoten) pp. 124-191

SUMMARY OF THE INVENTION

Problems to be Solved by the Invention

However, in the aforementioned Conventional Example 1, red tea or oolong tea in which tea material leaves are employed as a raw material is employed, and tea material leaves are employed alone. For this reason, quality is superior, but there is a problem in increased costs.

In the aforementioned Conventional Example 2, a large amount of tasty loquat tea can be produced, but the raw material thereof is only loquat leaves and does not include green tea components. For this reason, a green tea taste cannot be obtained.

In addition, in the aforementioned Conventional Example 3, high functional properties and good healthy properties are supposedly exhibited. However, as food for specified health use thereof, there is only Healthya® Green Tea commercially available from Kao Corporation. The aforementioned Healthya® Green Tea includes a larger amount of catechin than commercially available tea beverages. Since catechin is added to an extract of green tea, there is a problem in increased costs, and at the same time, an improvement in health cannot be observed as long as catechin intake is not large.

In addition, in general, the third crop of tea and the shutobancha are poor in quality and are cheap. For this reason, almost all thereof are clipped and junked, and a part thereof may be used as bancha (coarse tea).

The present invention has been completed after focusing attention on the aforementioned conventional problems. An objective of the present invention is to provide a composition having, as an active component, an extract contained in fermented tea obtained by tea-rolling processing of tea material leaves and loquat leaves in which unused resources of loquat leaves and tea material leaves are employed as raw materials. The aforementioned composition exhibits increased flavor with low costs, and provides a cooling aftertaste without astringency, as well as, exhibits effects of controlling the elevation of blood glucose levels, effects of controlling the occurrence of diabetes, effects of controlling body fat accumulation, effects of decreasing cholesterol levels and decreasing neutral fat levels in serum and the liver, and effects of decreasing serum lipid peroxides.

Means for Solving the Problems

In order to achieve the aforementioned objective, a fermented tea obtained by tea-rolling processing of tea material leaves and loquat leaves recited in Claim 1 is characterized in that the fermented tea is produced by primary-drying tea material leaves by means of a primary tea rolling dryer (primary drying step) to reduce the moisture content while stirring with hot air; subsequently, providing the primary-dried tea material leaves in a tea roller (tea rolling step); adding loquat leaves during the tea rolling step in order to knead loquat leaves together with the tea material leaves; and drying the kneaded tea material leaves and loquat leaves to carry out a drying step at the same time as stopping fermentation by inspiring hot air.

In addition, a fermented tea obtained by tea-rolling processing of tea material leaves and loquat leaves recited in Claim 2 is characterized in that, in the fermented tea obtained by tea-rolling processing of tea material leaves and loquat leaves according to Claim 1, in the aforementioned tea rolling step, the loquat leaves are added in an amount of 10 to 25% by weight based on the tea material leaves, and kneaded together with the tea material leaves for 15 to 25 minutes, followed by carrying out a fermentation step for 0 to 4 hours and the drying step at the same time as stopping the fermentation by inspiring hot air.

In addition, a fermented tea obtained by tea-rolling processing of tea material leaves and loquat leaves recited in Claim 3 is characterized in that, in the fermented tea obtained by tea-rolling processing of tea material leaves and loquat leaves according to Claim 1, in the aforementioned tea rolling step, the loquat leaves are added in an amount of 9 to 11% by weight based on the tea material leaves, and kneaded together with the tea material leaves for 15 to 25 minutes, followed by carrying out a fermentation step for 0 hours to 1 hour and the drying step at the same time as stopping the fermentation by inspiring hot air.

EFFECTS OF THE INVENTION

In the fermented tea recited in Claim 1, as described above, the fermented tea is produced by primary-drying tea material leaves by means of a primary tea rolling dryer (primary drying step) to reduce the moisture content while stirring with hot air; subsequently, providing the primary-dried tea material leaves in a tea roller (tea rolling step); adding loquat leaves during the tea rolling step in order to knead loquat leaves together with the tea material leaves; and drying the kneaded tea material leaves and loquat leaves to carry out a drying step at the same time as stopping fermentation by inspiring hot air. Thereby, the fermented tea obtained by tea-rolling processing of tea material leaves and loquat leaves can be produced, which is inexpensive, and in which flavor is more improved, and a cooling aftertaste is provided without astringency.

In addition, in the fermented tea recited in Claim 2, as described above, in the aforementioned tea rolling step, the loquat leaves are added in an amount of 10 to 25% by weight based on the tea material leaves, and kneaded together with the tea material leaves for 15 to 25 minutes, followed by carrying out a fermentation step for 0 to 4 hours and the drying step at the same time as stopping the fermentation by inspiring hot air. Thereby, the fermented tea obtained by tea-rolling processing of tea material leaves and loquat leaves can be produced, in which flavor is more improved, and a cooling aftertaste is provided without astringency.

In addition, in the fermented tea recited in Claim 3, as described above, in the fermented tea obtained by tea-rolling processing of tea material leaves and loquat leaves according to Claim 1, in the aforementioned tea rolling step, the loquat leaves are added in an amount of 9 to 11% by weight based on the tea material leaves, and kneaded together with the tea material leaves for 15 to 25 minutes, followed by carrying out a fermentation step for 0 hours to 1 hour and the drying step at the same time as stopping the fermentation by inspiring hot air. Thereby, the fermented tea can be produced, in which maltase or sucrase inhibiting properties which indicate effects of controlling the elevation of blood glucose levels are increased, compared to green tea leaves, loquat leaves, guava leaves, or red tea leaves, and at the same time, 1,1-dipicryl-2-phenylhydrazyl (DPPH) scavenging effects are exhibited, as well as, antioxidation effects approximately equivalent to the already known antioxidation effects of green tea can be exhibited.

In addition, it was confirmed by animal experimentation that a composition having an extract contained in the fermented tea leaves obtained by means of tea-rolling processing recited in Claim 3 exhibited effects of controlling the occurrence of diabetes, effects of controlling body fat accumulation, effects of reducing cholesterol levels and reducing neutral fats in serum and the liver, and effects of reducing serum lipid peroxides.

In addition, it was confirmed in animal experimentation that a composition having an extract contained in the fermented tea leaves obtained by means of tea-rolling processing produced by using the fermented tea recited in Claim 3 exhibited effects of controlling the elevation of glucose levels, effects of controlling the occurrence of diabetes, effects of controlling body fat accumulation, effects of reducing serum lipid peroxides, and effects of reducing the concentration of neutral fats in serum and the liver. The aforementioned effects are strong and cannot be observed in compositions including an extract from loquat leaves or crude tea obtained by only processing with tea material leaves in a tea making factory.

DETAILED DESCRIPTION OF THE INVENTION

Modes for carrying out the present invention are described with reference to the drawings.

Figure 1:
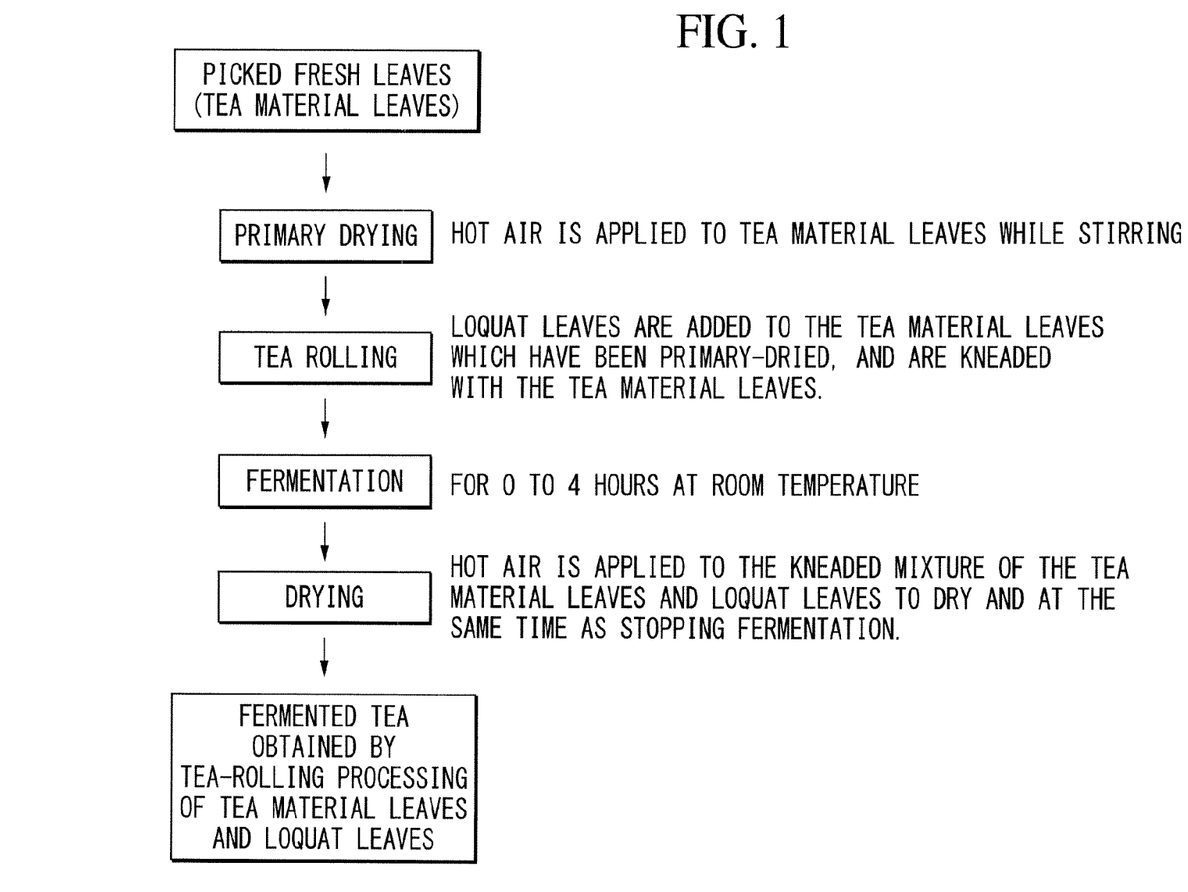
FIG. 1 is an illustrative diagram showing production steps of a fermented tea obtained by means of tea-rolling processing of tea material leaves and loquat leaves according to a mode for carrying out of the invention.

FIG. 1 is an illustrative diagram showing production steps of a fermented tea obtained by means of tea-rolling processing of tea material leaves and loquat leaves according to a mode for carrying out of the present invention.

Regarding taste and flavor, when the tea rolling period is 20 minutes and the fermentation period ranges from 0 to 4 hours, a superior flavor is provided, and a refreshing and superior aftertaste is provided. On the other hand, when the tea rolling period is 40 minutes, and the fermentation period is 6 or more hours, flavor is reduced, astringency becomes strong, and quality is degraded. Therefore, in order to pursue taste and flavor, it is preferable that the tea rolling period be 20 minutes and the fermentation period range from 0 to 4 hours.

The fermented tea is produced by primary-drying tea material leaves by means of a primary tea rolling dryer (primary drying step) to reduce the moisture content while stirring with hot air; subsequently, providing the primary-dried tea material leaves in a tea roller (tea rolling step); adding loquat leaves during the kneading step in order to knead loquat leaves together with the tea material leaves; subsequently, fermenting the mixture; and finally drying the fermented mixture to carry out a drying step at the same time as stopping fermentation by inspiring hot air. Thereby, a maltase or sucrase inhibiting rate which indicates effects of controlling the elevation of blood glucose levels is increased. When the amount of the added loquat leaves is increased with respect to the tea material leaves, the inhibiting rate is reduced. In addition, even if the tea rolling period is long, the inhibiting rate is also reduced. In addition, as the fermentation period is longer, the inhibiting rate is gradually reduced.

In addition, by employing the aforementioned production steps, 1,1-dipicryl-2-phenylhydrazyl (DPPH) scavenging effects which indicate antioxidation effects are increased. The antioxidation power is approximately equivalent to that of green tea in which there have been many reports about antioxidation effects.

Regarding taste and flavor, when the tea rolling period is 20 minutes, and the fermentation period ranges from 0 to 4 hours, a superior flavor is provided, and a cooling and superior aftertaste is provided. For this reason, in the case of dispensing as beverages, additives other than ascorbic acid, which is an antioxidant, may not be added.

In the following, Examples of the present invention are described.

Example 1

In the present example, 24 samples of the fermented tea obtained by means of tea-rolling processing of tea material leaves and loquat leaves, in total, were produced by employing 2 types of weight ratios, 10% and 25%, of loquat leaves with respect to tea material leaves of the third crop of tea; employing 2 types of tea rolling periods of 20 minutes and 40 minutes, by means of a tea roller; and employing 6 types of fermentation periods of 0 hours, one hour, 2 hours, 4 hours, 6 hours, and 24 hours.

The flavor and taste of the aforementioned 24 samples of the fermented tea obtained by means of tea-rolling processing of tea material leaves and loquat leaves were sensory evaluated by 3 panelists who had experience in sensory quality test of green tea. The results are shown in Table 1. Regarding taste and flavor, when the tea rolling period was 20 minutes, and the fermentation period ranged from 0 to 4 hours, a superior flavor was provided, and a cooling and superior aftertaste was provided. On the other hand, when the tea rolling period was 40 minutes and the fermentation period was 6 or more hours, the flavor was reduced, astringency became strong, and quality was degraded.

TABLE 1

| Blending ratio of loquat leaves, 10% | | | | | Blending ratio of loquat leaves, 25% | | | | |
|---|---|---|---|---|---|---|---|---|---|
| Tea rolling period (minutes) | Fermentation period (hours) | Flavor | Taste | Total | Tea rolling period (minutes) | Fermentation period (hours) | Flavor | Taste | Total |
| 20 | 0 | 3.0 | 3.0 | 6.0 | 20 | 0 | 3.0 | 3.7 | 6.7 |
|  | 1 | 3.0 | 3.0 | 6.0 |  | 1 | 3.0 | 3.0 | 6.0 |
|  | 2 | 2.7 | 3.0 | 5.7 |  | 2 | 3.0 | 3.0 | 6.0 |
|  | 4 | 2.7 | 3.0 | 5.7 |  | 4 | 3.3 | 2.7 | 6.0 |
|  | 6 | 2.0 | 2.7 | 4.7 |  | 6 | 2.0 | 2.0 | 4.0 |
|  | 24 | 1.0 | 1.3 | 2.3 |  | 24 | 1.0 | 1.3 | 2.3 |
| 40 | 0 | 3.0 | 2.3 | 5.3 | 40 | 0 | 2.7 | 2.7 | 5.4 |
|  | 1 | 2.3 | 2.3 | 4.6 |  | 1 | 2.7 | 2.3 | 5.0 |
|  | 2 | 2.3 | 2.7 | 5.0 |  | 2 | 3.0 | 2.3 | 5.3 |
|  | 4 | 2.7 | 2.3 | 5.0 |  | 4 | 2.3 | 2.7 | 5.0 |
|  | 6 | 3.0 | 1.7 | 4.7 |  | 6 | 3.0 | 2.7 | 5.7 |
|  | 24 | 1.0 | 1.3 | 2.3 |  | 24 | 1.0 | 1.0 | 2.0 |

In each of flavor and taste, the perfect score is 5 points.

In sensory quality test of green tea, in the case of the first crop of tea, 6 to 7 points were obtained; in the case of the second crop of tea, approximately 5 points were obtained; and in the case of the third crop of tea, 5 points were obtained.

An AGH inhibiting property (maltase and sucrase inhibiting property) of the fermented tea obtained by tea-rolling processing of tea material leaves and loquat leaves (sample concentration=2.0 mg/ml) was measured. Regarding the maltase and sucrase inhibiting rate which indicates an effect of controlling the elevation of blood glucose levels, when the amount of the blended loquat leaves was increased with respect to the tea material leaves, the inhibiting rate was reduced. Even if the tea rolling period was increased, the inhibiting rate was also reduced. In addition, as the fermentation period was increased, the inhibiting rate was reduced.

TABLE 2

| Blending ratio of loquat leaves, 10% | | | | Blending ratio of loquat leaves, 25% | | | |
| --- | --- | --- | --- | --- | --- | --- | --- |
| Tea rolling period (minutes) | Fermentation period (hours) | Maltase inhibiting rate (%) | Sucrase inhibiting rate (%) | Tea rolling period (minutes) | Fermentation period (hours) | Maltase inhibiting rate (%) | Sucrase inhibiting rate (%) |
| 20 | 0 | 81.9 | 82.7 | 20 | 0 | 70.3 | 61.9 |
|  | 1 | 72.3 | 67.6 |  | 1 | 66.3 | 53.6 |
|  | 2 | 65.4 | 60.4 |  | 2 | 62.0 | 46.9 |
|  | 4 | 59.3 | 45.1 |  | 4 | 58.6 | 40.6 |
| 40 | 0 | 66.9 | 43.4 | 40 | 0 | 69.6 | 57.5 |
|  | 1 | 56.3 | 36.7 |  | 1 | 58.5 | 38.9 |
|  | 2 | 56.9 | 32.0 |  | 2 | 55.2 | 37.9 |
|  | 4 | 54.1 | 35.7 |  | 4 | 49.6 | 28.4 |

| Sample | Maltase inhibiting rate (%) | Sucrase inhibiting rate (%) |
| --- | --- | --- |
| Green tea | 61.2 | 61.3 |
| Loquat leaves | 55.4 | 58.5 |
| Guava tea | 48.3 | 38.3 |
| Red tea | 55.6 | 52.7 |

The activities of eliminating DPPH radicals of the fermented tea (sample concentration=2.0 mg/ml) obtained by tea-rolling processing of loquat leaves and tea material leaves were measured. The results are shown in Table 3. The activities of eliminating DPPH radicals were increased for the tea rolling period of 20 minutes and for the fermentation period of 0 hours.

TABLE 3

| Blending ratio of loquat leaves, 10% | | | Blending ratio of loquat leaves, 25% | | |
| --- | --- | --- | --- | --- | --- |
| Tea rolling period (minutes) | Fermentation period (hours) | Eliminating activity (µmol-Trolox/mg) | Tea rolling period (minutes) | Fermentation period (hours) | Eliminating activity (µmol-Trolox/mg) |
| 20 | 0 | 1.5 | 20 | 0 | 1.5 |
|  | 2 | 1.1 |  | 1 | 0.9 |
|  | 6 | 0.8 |  | 2 | 0.8 |
| 40 | 0 | 1.4 | 40 | 0 | 1.2 |
|  | 2 | 0.8 |  | 1 | 1.1 |
|  | 6 | 0.9 |  | 2 | 0.7 |

| Sample | Eliminating activity (µmol-Trolox/mg) |
| --- | --- |
| Green tea | 1.6 |
| Loquat leaves | 0.3 |
| Guava tea | 1.1 |

In the following, the effects of Example 1 are described.

In Example 1 of the present invention, the effects described below can be obtained.

Recently, the price of the third crop of tea among the tea material leaves has greatly reduced, and a comparatively large amount of tea leaves also including the shuto-bancha and the skiffed leaves of tea have been junked. In addition, the unit price of loquats tends to be reduced due to competition from low-cost import fruits or an economic slump. Loquat leaves have been partially sold as loquat tea, but many loquat leaves have not been utilized. In order to utilize active components such as polyphenols included in the aforementioned non-utilized tea leaves and loquat leaves, focusing on the mixing ratio, the tea rolling period, and the fermentation period has lead to the development of the novel tea manufacturing technique, as described above. In the novel technique, commercial products exhibiting increased functional properties, compared to green tea or loquat leaf tea known as being good for health, can be developed. For this reason, differentiation from the conventional tea beverages or imported tea can be performed, and therefore, the novel technique can contribute to enhance the competitive powers of tea producers and dependent business.

In the following, another example of the present invention is described.

Example 2

In Example 2, by adding loquat leaves to tea material leaves, and fermenting the mixture in test tubes, the comparison of the production of catechins, theaflavins, and theasinensins was carried out.

Three model experiments A, B, and C of tea leaf fermentation described below were carried out, and the comparison of theaflavin production and reduction of catechin was carried out.

A: 50 g of fresh tea leaves was pulverized together with 250 mL of water in a waring blender, and the mixture was placed in a polybeaker (1 L), and was stirred for 2 hours by mixing the air into the mixture under rapid rotation by means of a stirrer equipped with a shaft having propeller type rotor blades with a size of 5 cm. 0 minutes, 15 minutes, 30 minutes, 60 minutes, and 120 minutes after commencing stirring, 5.0 mL of the reaction mixture was brought out, and washed with water (approximately 20 mL) in a conical flask (50 mL). Subsequently, heating for approximately 20 seconds was carried out by means of a microwave oven. After cooling, ethanol was added thereto to make the overall volume 50 mL. The mixture was filtered by means of a membrane filter (0.45 μm), followed by analyzing 10 μL thereof by means of high performance liquid chromatography (HPLC). The analysis conditions were as follows: column=Cosmosil $5C_{18}$ ARII (4.6× 250 mm); column temperature=35° C.; mobile phase=A: 50 mM phosphoric acid, B: $CH_3CN$, B from 4% to 30% (for 39 minutes), and from 30% to 75% (for 15 minutes); flow rate=0.8 mL/min; and detection=photodiode array detection (max absorbance).

B: 50 g of fresh tea leaves and 0.25 g of chlorogenic acid were pulverized together with 250 mL of water in a waring blender, and the mixture was placed in a polybeaker (1 L), and was stirred for 2 hours in the same manner as described above. 0 minutes, 15 minutes, 30 minutes, 60 minutes, and 120 minutes after commencing stirring, the reaction mixture was subjected to analysis by means of HPLC in the same manner as described above.

C: 50 g of fresh tea leaves and 5 g of fresh loquat leaves were pulverized together with 250 mL of water in a waring blender, and the mixture was placed in a polybeaker (1 L), and was stirred for 2 hours in the same manner as described above. 0 minutes, 15 minutes, 30 minutes, 60 minutes, and 120 minutes after commencing stirring, the reaction mixture was subjected to analysis by means of HPLC in the same manner as described above. The content of caffeoylquinic acid (chlorogenic acid and isomers thereof) in the fresh loquat leaves used here was approximately 0.7%.

Figure 2:
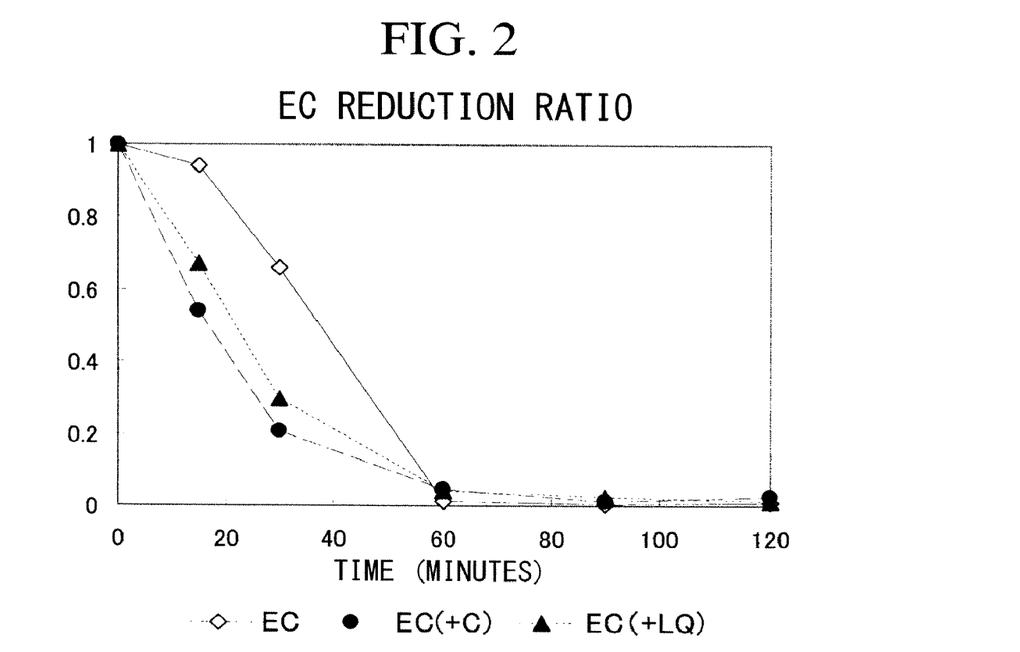
FIG. 2 is a graph showing a reduction ratio of epicatechin (hereinafter referred to as EC) during fermentation of tea leaves, in which +C and +LQ indicate an EC reduction ratio in the case of coexisting chlorogenic acid during the fermentation and an EC reduction ratio in the case of coexisting fresh loquat leaves during the fermentation, respectively.
Figure 3:
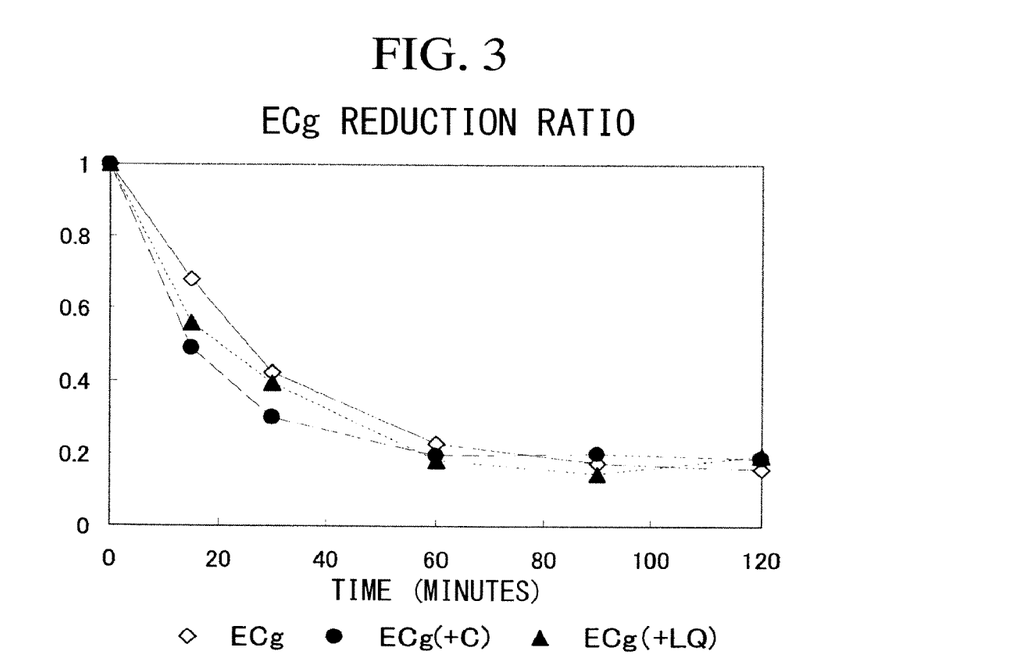
FIG. 3 is a graph showing a reduction ratio of epigallocatechin (hereinafter referred to as EGC) during fermentation of tea leaves, in which +C and +LQ indicate an EC reduction ratio in the case of coexisting chlorogenic acid during the fermentation and an EC reduction ratio in the case of coexisting fresh loquat leaves during the fermentation, respectively.
Figure 4:
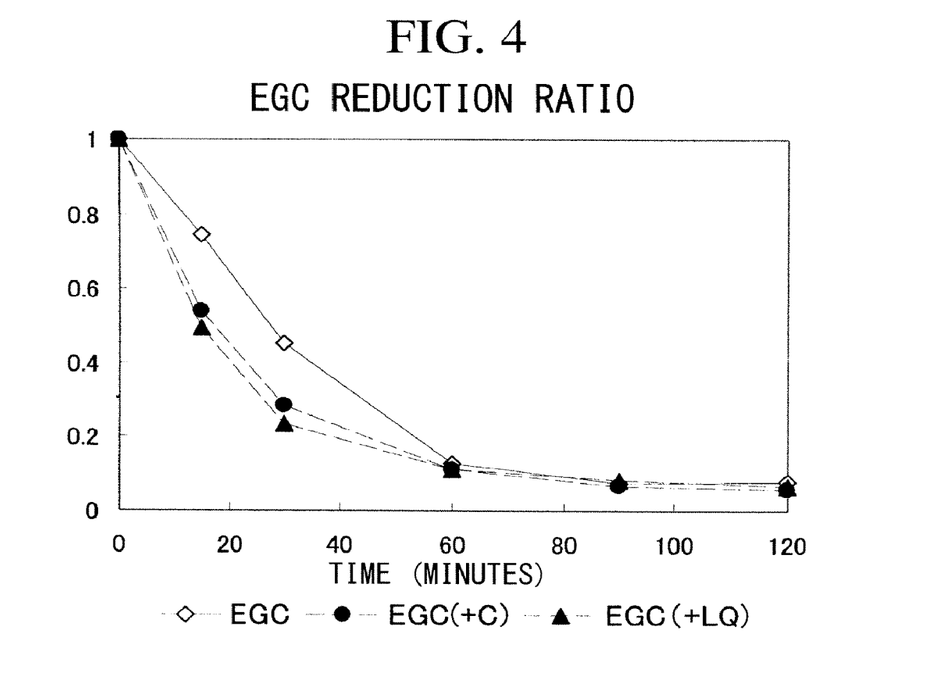
FIG. 4 is a graph showing a reduction ratio of epicatechin gallate (hereinafter referred to as ECg) during fermentation of tea leaves, in which +C and +LQ indicate an EC reduction ratio in the case of coexisting chlorogenic acid during the fermentation and an EC reduction ratio in the case of coexisting fresh loquat leaves during the fermentation, respectively.
Figure 5:
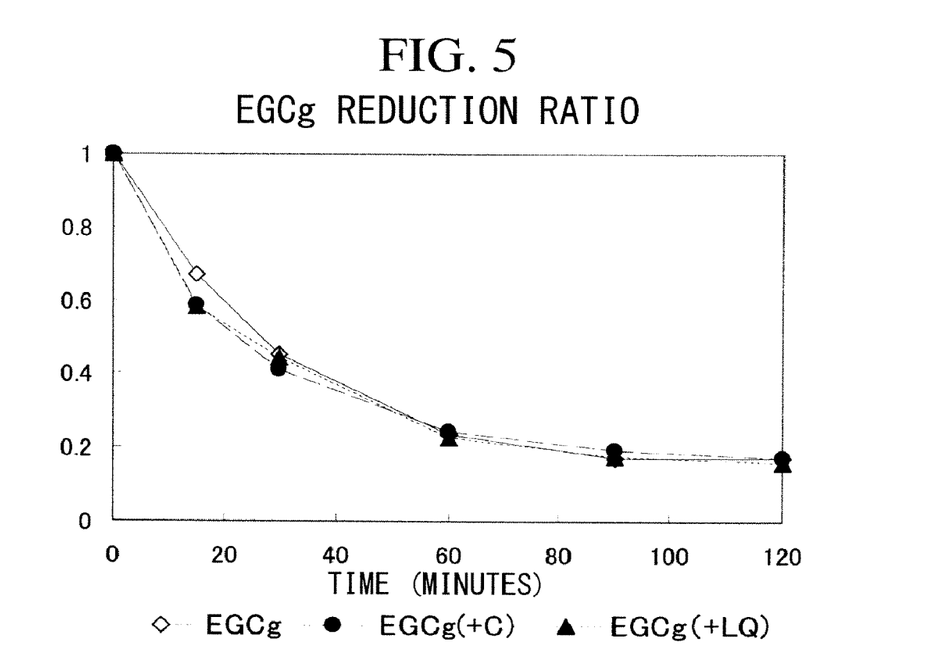
FIG. 5 is a graph showing a reduction ratio of epigallocatechin gallate (hereinafter referred to as EGCg) during fermentation of tea leaves, in which +C and +LQ indicate an EC reduction ratio in the case of coexisting chlorogenic acid during the fermentation and an EC reduction ratio in the case of coexisting fresh loquat leaves during the fermentation, respectively.
Figure 6:
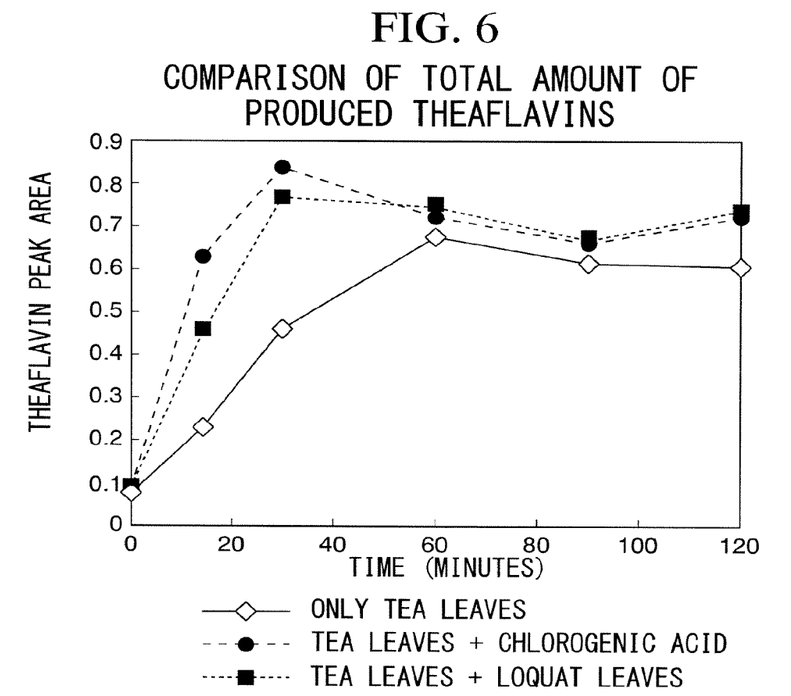
FIG. 6 is a graph showing changes over time in a peak area of theaflavins produced during fermentation of tea leaves.
Figure 7:
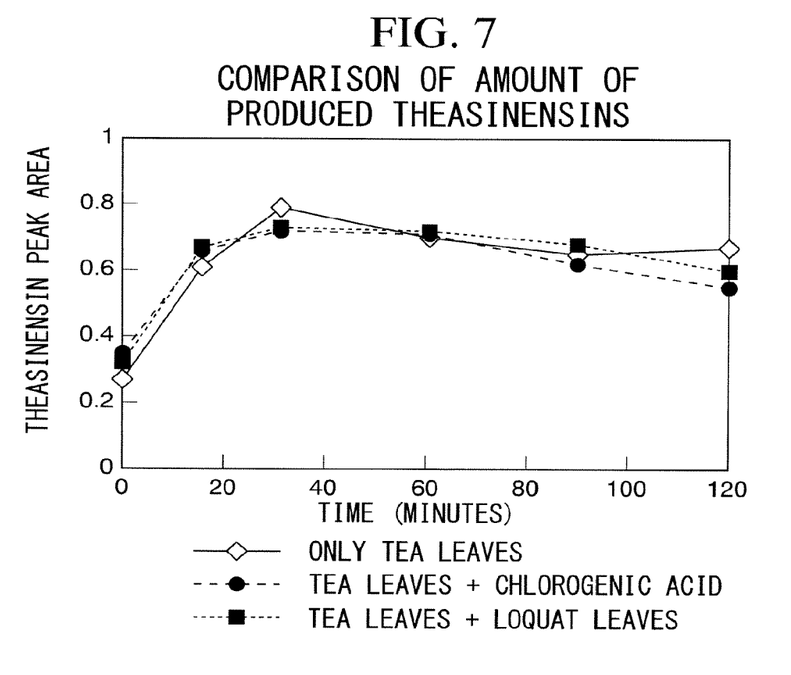
FIG. 7 is a graph showing changes over time in a peak area of theasinensins produced during fermentation of tea leaves.

By adding chlorogenic acid and loquat leaves, oxidations of EC (FIG. 2), EGC (FIG. 3), and ECg (FIG. 4) were accelerated at the initial period of fermentation. Acceleration of oxidation of EGCg (FIG. 5) was poor. The production of theaflavin was accelerated by adding chlorogenic acid and loquat leaves (FIG. 6). The produced amount of theasinensins was not affected thereby (FIG. 7). It was speculated that the aforementioned acceleration of oxidation occurred due to the so-called conjugate oxidation mechanism, that is, chlorogenic acid being first enzymatically oxidized, and the quinone product produced therefrom oxidizing other catechins, and thereby, oxidation being accelerated.

From the results (Table 2) of the AGH inhibiting properties (maltase and sucrase inhibiting properties) of the fermented tea obtained by tea-rolling processing of tea material leaves and loquat leaves carried out in Example 1, and the aforementioned amounts of the produced catechins, theaflavins, and theasinensins, the following speculation can be carried out.

Tea material leaves contain a large amount of catechins (EC, EGC, ECg, and EGCg). In this case, the ratio of inhibiting maltase and sucrase of the fermented tea obtained by tea-rolling processing of tea material leaves and loquat leaves (blending ratio of loquat leaves=10%, tea rolling period=20 minutes, and fermentation period=0 hours) is increased by approximately 20%, compared to that of green tea. For this reason, it is speculated that the ratio of inhibiting maltase and sucrase is not effected by catechins. In addition, by adding loquat leaves to tea material leaves, theaflavins are produced. The amount of the produced theaflavins reaches a peak at 30 minutes, and subsequently, remains at the same level. In the fermented tea obtained by tea-rolling processing of tea material leaves and loquat leaves (blending ratio of loquat leaves=10%, and fermentation period=0 hours), the fermented tea obtained from the tea rolling period of 40 minutes has a larger amount of theaflavins than the fermented tea obtained from the tea rolling period of 20 minutes. However, the fermented tea obtained from the tea rolling period of 20 minutes has a 15% higher ratio of inhibiting maltase and has approximately a 40% higher ratio of inhibiting sucrase than those of the fermented tea obtained from the tea rolling period of 40 minutes. For this reason, it is speculated that the ratio of inhibiting maltase and sucrase is not effected by theaflavins. In addition, the amount of the produced theasinensins in the case of the fermented tea of only tea material leaves is not different from that in the case of the fermented tea obtained by tea-rolling processing of tea material leaves and loquat leaves. For this reason, it can be speculated that the ratio of inhibiting maltase and sucrase is not effected by theasinensins. From the aforementioned speculations, by adding loquat leaves to tea material leaves, and subjecting the mixture to tea-rolling processing, substances other than catechins, theaflavins, and theasinensins, which are generally known as functional substances, may be produced. In other words, new components exhibiting high functional properties which green tea, red tea, or loquat tea does not exhibit may be produced.

In the following, the effects of Example 2 are described.

In Example 2 of the present invention, the following effects can be obtained.

By adding loquat leaves, the production of catechin oxidation products having strong activities of inhibiting glycolytic enzymes is accelerated, and at the same time, reduction of the kneading period or fermentation period can be established, as well as, reduction of the production period and cost cutting can be carried out.

Example 3

In Example 3, green tea produced from tea material leaves, red tea leaves, loquat tea produced by drying and roasting loquat leaves, and fermented tea obtained by tea-rolling processing of tea material leaves and loquat leaves were compared in view of flavor components, and the aroma components specified in the fermented tea obtained by tea-rolling processing of tea material leaves and loquat leaves were studied. In general, preprocessing of the tea-based flavor components is carried out by means of a column adsorption method. Here, as a chromatography measurement method of simple and rapid extraction and concentration of a sample, a solid microextraction method was employed although the number of peaks for detecting flavor components was not many.

The sample was prepared as follows. In a Bayer bottle with a volume of 50 mL, 2.5 g of each of green tea, red tea, loquat tea, and fermented tea obtained by tea-rolling processing, 0.1 mL of a 30% aqueous solution of sodium chloride, and 20 mL of distilled water at 80.degree. C. were placed, and tightly capped. Subsequently, the mixture was heated for 5 minutes at 80.degree. C. to make inside the Bayer bottle stable. Subsequently, a trap tube was inserted thereinto for 20 minutes, and the generated flavor components were trapped. The trap tube in which the generated flavor components were trapped was inserted in an inlet of gas chromatograph heated to 250.degree. C., and the flavor components were introduced into the column of the gas chromatograph for 3 minutes to carry out analysis. As the trap tube, a polydimethylcyclohexane/carboxen/divinylbenzene trap tube manufactured by SUPELCO Co., Ltd, was employed. Regarding the analysis conditions of the gas chromatograph, a stabil WAX (polyethylene-based) having a size of 60 m.times.0.25 mm with a film thickness of 0.25.mu., manufactured by Reapect Co., Ltd., as the column, were employed, and the temperature of the column was maintained for 3 minutes at 70.degree. C., and was increased up to 250.degree. C. at the rate of 2.degree. C./minute. The temperature of the inlet was 250.degree. C., and helium pressure was 120 kPa. With respect to gas chromatograph mass analysis for identification of components, an I/F temperature of 250.degree. C., an ionization voltage of 70 eV, and an ionization current of 60.mu.A were employed.

The identified flavor components of the green tea, fermented tea obtained by tea-rolling processing, red tea, and loquat tea are shown in Table 4. Pyridine and pyrrole based components which were produced by roasting were removed from the results of analysis. Regarding the number of the identified flavor components, green tea had 45 components, loquat tea had 24 components, the fermented tea obtained by tea-rolling processing had 37 components, and red tea also had 37 components. The components identified only in green tea among green tea, fermented tea obtained by tea-rolling processing, red tea, and loquat tea were 11 components, namely, consisting of acetone, 1-pentanol, octanal, 2,5-hexadiene, 2-methyl-2-hexen-5-one, 1-tetradecene, 1-octen-3-ol, decanal, 1-octanol, alpha-terpineol, and geraniol acetone. The components identified only in fermented tea obtained by tea-rolling processing were two components, namely, consisting of 3-hexane-1-ol butyrate and 3-methyl-2-(2-pentenyl)-2-cyclopenten-1-one. The components identified only in red tea were 6 components, namely, consisting of limonene, ocimene, 4,8-dimethyl-1,3,7-nonatriene, 7,10-dimethyl-3-methylene-1,5,10-dodecatriene, 1,2-dihydro-1,5,8-trimethylnaphthalene, and ortho-hydroxycinnamic acid. The components identified only in loquat tea were 2 components, namely, consisting of safranal and 2-hexanic acid. In addition, the components contained in both fermented tea obtained by tea-rolling processing and red tea were 26 components which corresponded to approximately ⅔ of all the components. As described above, in accordance with sensory tests, flavors are different between red tea produced by fermentation of only the same tea material leaves as green tea, and fermented tea obtained by adding loquat leaves to tea material leaves and subjecting to fermentation. This result may be caused by the different compositions of the flavor components, that is, the differences between the components included only in red tea and the components included only in the fermented tea obtained by tea-rolling processing.

TABLE 4

| Component name | Green tea | Fermented tea obtained by tea-rolling processing | Red tea | Loquat tea |
| --- | --- | --- | --- | --- |
| Dimethyl sulfide | ◯ | ◯ | ◯ | |
| Acetone | ◯ | | | |
| Isobutanal | | ◯ | ◯ | ◯ |
| Methyl acetate | | ◯ | ◯ | ◯ |
| 2-methyl-butanal | ◯ | ◯ | ◯ | ◯ |
| 3-methyl-butanal | ◯ | ◯ | ◯ | ◯ |
| Pentanal | ◯ | ◯ | | |
| 2,3-pentadione | | | ◯ | ◯ |
| Hexanal | ◯ | ◯ | ◯ | ◯ |
| Beta-myrcene | ◯ | ◯ | ◯ | |
| Heptanal | ◯ | ◯ | | |
| n-dodecane | | | ◯ | ◯ |
| Limonene | | | ◯ | |
| 2-hexanal | ◯ | ◯ | | ◯ |
| 1-pentanol | ◯ | | | |
| Ocimene | | | ◯ | |
| Octanal | ◯ | | | |
| 4,8-dimethyl-1,3,7-nonatriene | | | ◯ | |
| 3-hexen-1-ol acetate | ◯ | ◯ | | ◯ |
| 2,5-hexadiene | ◯ | | | |
| 2-methyl-2-hexen-5-one | ◯ | | | |
| 3-hexen-1-ol | ◯ | ◯ | ◯ | ◯ |
| Nonanal | ◯ | | | |
| 1-tetradecene | | ◯ | ◯ | ◯ |
| 1-octen-3-ol | ◯ | | | |
| trans-linalool oxide | ◯ | ◯ | ◯ | |
| 3-hexen-1-ol buryrate | | ◯ | | |
| 2-methylbutyric acid, 3-hexen-1-ol | ◯ | ◯ | ◯ | |
| Furfural | | | ◯ | ◯ |
| cis-linalool oxide | ◯ | ◯ | ◯ | |
| Decanal | ◯ | | | |
| 2,4-heptadienal | ◯ | ◯ | | |
| Linalool | ◯ | ◯ | ◯ | |
| 1-octanol | ◯ | | | |
| Benzaldehyde | ◯ | ◯ | ◯ | ◯ |
| 5-methyl-furfural | | | ◯ | ◯ |
| 2-hexen-1-ol butyrate | ◯ | ◯ | ◯ | |
| 3-hydroxy-3,7-dimethyl-1,5,7-octatriene | ◯ | ◯ | | |
| Beta-cyclocitral | ◯ | ◯ | | ◯ |
| Caproic acid, 3-hexen-1-ol | ◯ | ◯ | ◯ | ◯ |
| 7,10-dimethyl-3-methylene-1,6,10-dodecatriene | | | ◯ | |
| Benzene acetoaldehyde | ◯ | ◯ | | ◯ |
| Safranal | | | | ◯ |
| Alpha-terpineol | ◯ | | | |
| Alpha-farnesene | ◯ | ◯ | ◯ | |
| Epoxylinalol | ◯ | ◯ | ◯ | |
| 1,2-dihydro-1,5,8-trimethylnaphthalene | | | ◯ | |
| Methyl salicylate | ◯ | ◯ | ◯ | ◯ |
| Geraniol | ◯ | ◯ | ◯ | |
| Geraniol acetone | ◯ | | | |
| Benzyl alcohol | ◯ | ◯ | ◯ | |
| 2-phenylethanol | ◯ | ◯ | ◯ | |
| 3-hexenic acid | | | | ◯ |
| 2-hexenic acid | | | | ◯ |
| Benzylnitrile | ◯ | ◯ | ◯ | ◯ |
| Beta-ionone | ◯ | ◯ | | ◯ |
| 3-methyl-2-(2-pentenyl)-2-cyclopenten-1-one | | ◯ | | |
| Nerolidol | ◯ | ◯ | ◯ | |
| 3-hexen-1-ol benzoate | ◯ | ◯ | ◯ | |
| 3,5-di(tetrabutyl)-phenol | ◯ | ◯ | ◯ | ◯ |
| Ortho-hydroxy-cinnamic acid | | | ◯ | |
| Indole | ◯ | ◯ | ◯ | |

◯: detected flavor component

In the following, the effects of Example 3 are described.

In Example 3 of the present invention, the effects described below can be obtained.

Red tea produced by fermentation of only the same tea material leaves as green tea has a different composition of flavor components from that of the fermented tea obtained by means of tea-rolling processing in which loquat leaves are blended with tea material leaves, and the mixture is subjected to fermentation. In other words, by means of blending loquat leaves with tea material leaves, kneading loquat leaves together with tea material leaves, and fermenting the mixture, a flavor which is different from that of red tea can be provided.

Example 4

In Example 4, in order to study the functional properties of a composition having, as an active component, an extract contained in the fermented tea obtained by means of tea-rolling processing of tea material leaves and loquat leaves, produced in Example 1 (from the results shown in Table 2, an increased ratio of inhibiting maltase and sucrase was exhibited; blending rate of loquat leaves=10%, tea rolling period=20 minutes, and fermentation period=0 hours), experiments were carried out on animals with a single administration.

Tea leaves in the form of a powder may be taken, but in general, tea leaves are extracted with hot water, and the extract is drunk in many cases. Therefore, in order to study the functional properties of an extract obtained by extracting the fermented tea leaves obtained by means of tea-rolling processing of tea material leaves and loquat leaves produced in Example 1, with hot water, experiments were carried out on animals with a single administration.

Figure 8:
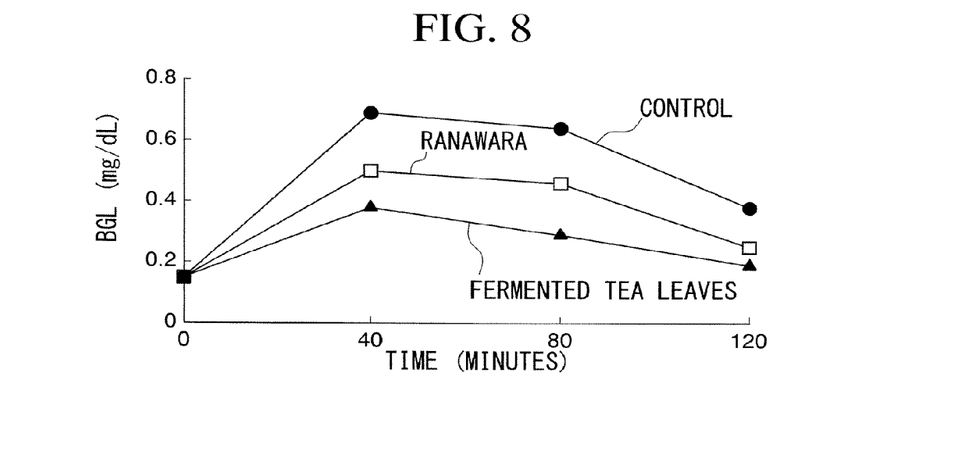
FIG. 8 is a graph showing changes in blood glucose levels in rats up to 120 minutes from administration of an extract of a fermented tea obtained by means of tea-rolling processing which was produced in Example 4 with hot water, and administration of an extract of RANAWARA, which is a plant in Sri Lanka and is reported as having increased effects of controlling the elevation of blood glucose levels, the extract being produced by extracting RANAWARA with methanol, concentrating the extract, freeze-drying the concentrated extract, and dissolving the freeze-dried product in water.

Maltose was administrated to a normal rat at a dosage of 2 g per kg of the body weight. Subsequently, an extract obtained by extracting the fermented tea obtained by means of tea-rolling processing with hot water was administered to the rat at a dosage of 20 mg per kg of the body weight, or a product was administered to the rat at a dosage of 20 mg per kg of the body weight, in which a plant in Sri Lanka, one of the materials having high activities with the highest level among the materials reported heretofore (J. Agri. Food. Chem. 2004) was extracted with methanol, then concentrated, and then freeze-dried, followed by dissolving the freeze-dried product in water. 30 minutes, 60 minutes, and 120 minutes after the administration, the blood glucose levels were measured. Changes in the blood glucose levels are shown in FIG. 8. It was observed that the extract obtained by extracting the fermented tea obtained by means of tea-rolling processing with hot water exhibited increased effects of controlling the elevation of blood glucose levels, compared to the plant, RANAWARA, in Sri Lanka which is one of the materials having high activities with the highest levels among the materials reported heretofore (J. Agri. Food. Chem. 2004).

As an indication of 50% reduction of the elevation of blood glucose levels, EC50 is employed. EC50 of RANAWARA and acarbose taken as an oral medicine for treating diabetes by type 2 diabetes subjects are shown in Table 5. It was observed that the extract obtained by extracting the fermented tea obtained by means of tea-rolling processing with hot water exhibited increased effects of controlling the elevation of blood glucose levels, compared to RANAWARA, and for this reason, the extract of the aforementioned fermented tea exhibited effects which were equivalent to those of the medicine.

TABLE 5

| | $EC_{50}$ (mg/kg) |
|---|---|
| Acarbose | 3.1 |
| RANAWARA | 4.9 |

Maltose was administrated to a normal rat at a dosage of 2 g per kg of the body weight. Subsequently, an extract obtained by extracting the fermented tea obtained by means of tea-rolling processing with hot water was administered at a dosage of 10 mg per kg of the body weight or 20 mg per kg of the body weight. A decreasing rate of the total blood glucose level area up to 120 minutes after carrying out carbohydrate load (AUCO-120) is shown in Table 6. Assessing based on AUC, in the case of administering 10 mg/kg of the extract obtained by extracting high-functional tea leaves with hot water, 21.9% of BGL controlling effects were observed, and in the case of administering 20 mg/kg of the extract, 36.8% of BGL controlling effects were observed. Consequently, clear content-dependence properties were exhibited. Assessing from appearances of the aforementioned effects at the dosage levels described above, it is believed that the aforementioned extract is an extremely increased active material which has not been known.

TABLE 6

| Concentration of extract | Area of total blood glucose level (AUCO-120) | Reduction rate of area of total blood glucose level (%) |
|---|---|---|
| Control | 130.5 ± 4.8 mg/h/dL | — |
| 10 mg/kg | 102.5 ± 12.8 mg/h/dL | 21.9 |
| 20 mg/kg | 82.5 ± 6.5 mg/h/dL | 36.8 |

In the following, the effects of Example 4 are described.

In Example 4 of the present invention, the effects described below can be obtained.

A composition having, as an active component, the extract contained in the tea leaves obtained by means of tea-rolling processing which are produced by a new tea manufacturing technique based on the mixing ratio, tea rolling period, and fermentation period employing the tea material leaves which are conventionally junked and the loquat leaves which were not conventionally utilized effectively, can effectively control blood glucose levels, and can be expected to be employed for the treatment and prevention of diabetic subjects or would-be subjects thereof. In addition, the composition can contribute to competitiveness of tea producers, loquat leaf producers, and dependent business.

Example 5

In Example 5, in order to study the functional properties of a composition having, as an active component, an extract contained in the fermented tea leaves obtained by means of tea-rolling processing of tea material leaves and loquat leaves, produced in Example 1 (from the results shown in Table 2, an increased ratio of inhibiting maltase and sucrase was exhibited; blending rate of loquat leaves=10%, tea rolling period=20 minutes, and fermentation period=0 hours), experiments were carried out on animals in which administration was carried out for a long time.

The fermented tea leaves obtained by means of tea-rolling processing of tea material leaves and loquat leaves produced in Example 1 were subjected to pulverization processing by means of a food processor until powder having a size ranging from 60 to 100 meshes was obtained. The powdery fermented tea leaves were fed to rats. In addition, as comparative examples, the unrefined tea leaves (crude tea) in which the same tea material leaves as described above were employed and were subjected to processing in a tea factory, or the powdery loquat leaves in which dried loquat leaves were subjected to pulverization processing were fed to rats.

Male Otsuka Long-Evans Tokushima Fatty rats (hereinafter, referred to as OLETF rats) at the age of one month in which type 2 diabetes spontaneously occurred, and male Long-Evans Tokushima Otsuka rats (hereinafter, referred to as LETO rats) which were subject model animals and did not develop diabetes were employed. The rats were bred in an animal room at room temperature of 22±1° C., with a light cycle of lighting from 8:00 to 20:00.

For the first to third months, the LETO rats and OLETF rats were subjected to pre-rearing by feeding an MF solid diet. In the OLETF rats, type 2 diabetes commonly occurred between 5 and 8 months of age. For this reason, the test diet feeding was started in the LETO rats and the OLETF rats at the age of 4 months which was one month before the possibility of an occurrence of diabetes.

At the age of 4 months, after fasting for 6 hours (9:00 to 15:00), the blood glucose level was measured by taking the blood from a tail vein. The rats were divided into groups, one group having 6 rats, so that they have the same body weight and the same blood glucose levels. The grouped rats were freely fed with the test diet described below for 5 months.

The test diet in which a refined diet based on AIN-76 was employed as a control diet was fed to each of the control groups of the LETO rats and the OLETF rats. The diet had a composition based on weight (g/kg) consisting of 200 of casein, 100 of cooking oil, 35 of a mineral mixture (AIN-76-MX), 10 of a vitamin mixture (AIN-76-VX), 50 of cellulose, 2 of choline bitartrate, 3 of DL-methionine, 150 of cornstarch, and 450 of sucrose. In the groups for adding powder leaf samples, the powder leaf sample was added in an amount of 5% with respect to the total weight of the diet, and sucrose was reduced in the same amount as that of the added powder leaf sample. During the rearing period, the amount of the diet was measured every day, and the body weight and the amount of water taken by the rats were measured every other day.

After 1, 2, 3, 4, and 5 months from starting administration of the test diet, the blood glucose levels were measured by means of a Medisafe Chip for monitoring blood glucose (Terumo Corporation, in Tokyo) by taking the blood from a tail vein after fasting for 6 hours. The changes in the blood glucose levels of the rats for 5 months are shown in FIG. 9.

Figure 9:
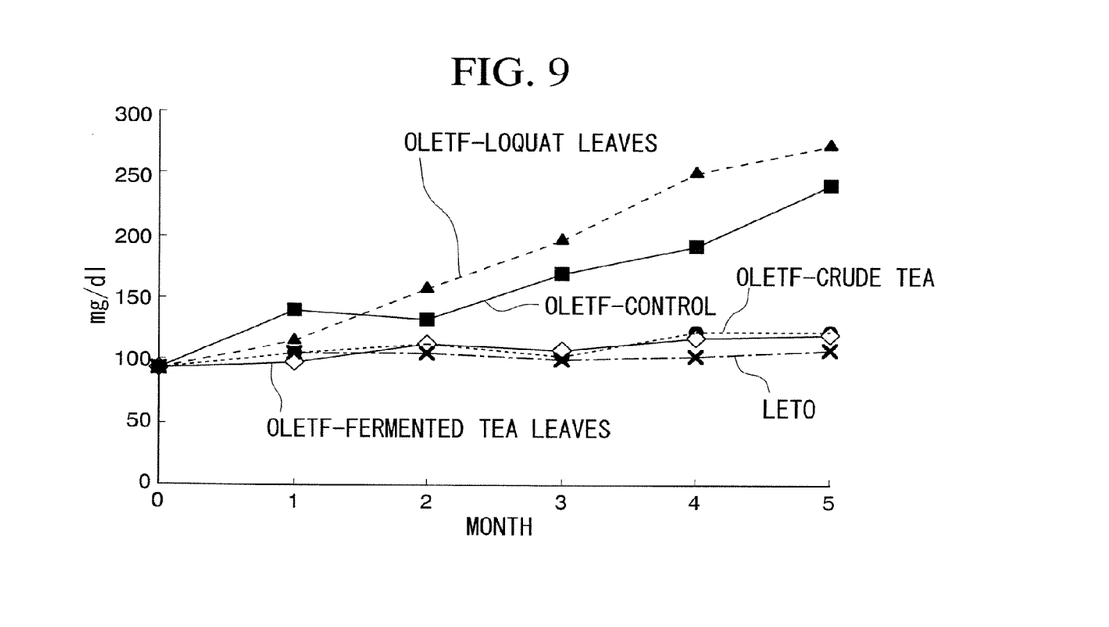
FIG. 9 is a graph showing changes in blood glucose levels in rats in which a fermented tea obtained by means of tea-rolling processing which was produced in Example 5 was fed.

As shown in FIG. 9, the blood glucose levels of the LETO rats in which the control diet was fed and diabetes did not occur was low over the rearing period. In contrast, the blood glucose level of the OLETF rats in which the control diet was fed and diabetes occurred was generally increased over time, and occurrences of diabetes were observed. In addition, the blood glucose level of the OLETF rats in which the diet with powdery loquat leaves was fed was also generally increased over time, in the same manner as that of the OLETF rats in which the control diet was fed. However, the blood glucose level of the OLETF rats in which the diet with powdery crude tea or the diet with powdery fermented tea leaves obtained by tea-rolling processing was fed was not increased over time and was approximately the same low level as that of the LETO rats. From the results described above, it is shown that the powdery crude tea and the powdery fermented tea leaves obtained by tea-rolling processing exhibit superior effects of controlling the elevation of blood glucose levels.

The serum insulin levels of the OLETF rats in which the control diet was fed or the diet with the powdery loquat leaves was fed were reduced after 5 months by the occurrence of diabetes. In contrast, the serum insulin levels of the OLETF rats in which the diet with the powdery crude tea or the diet with the powdery fermented tea leaves obtained by tea-rolling processing was fed were increased to the same level as that of the LETO rats. The results are shown in Table 7. Therefore, it was observed that the powdery crude tea or the powdery fermented tea leaves obtained by tea-rolling processing could improve the reduction of insulin secretion caused by the occurrence of diabetes.

TABLE 7

| Sample | Insulin level (ng/ml) |
| --- | --- |
| LETO - control diet | 7.30 |
| OLETF - control diet | 3.68 |
| OLETF - diet with powdery crude tea | 8.18 |
| OLETF - diet with powdery loquat leaves | 3.12 |
| OLETF - diet with powdery fermented tea leaves obtained by tea-rolling processing | 7.75 |

The serum lipid peroxide levels of the OLETF rats in which the powdery crude tea or the powdery loquat leaves were fed were highly increased after 5 months. In contrast, the serum lipid peroxide level of the OLETF rats in which the powdery fermented tea leaves obtained by tea-rolling processing were fed was low. The results are shown in Table 8. Therefore, it is suggested that the powdery fermented tea leaves obtained by tea-rolling processing can reduce the serum lipid peroxide levels.

TABLE 8

| Sample | Serum lipid peroxide level (nmol/ml) |
| --- | --- |
| LETO - control diet | 11.86 |
| OLETF - control diet | 63.78 |
| OLETF - diet with powdery crude tea | 92.83 |
| OLETF - diet with powdery loquat leaves | 78.57 |
| OLETF - diet with powdery fermented tea leaves obtained by tea-rolling processing | 35.23 |

The weights of adipose tissues around the testes and of the kidneys of the OLETF rats in which the powdery crude tea, the powdery loquat leaves, or the powdery fermented tea leaves obtained by tea-rolling processing were fed were significantly reduced, compared to that of the OLETF rats in which the control diet was fed. For this reason, it is shown that the powdery crude tea, the powdery loquat leaves, and the powdery fermented tea leaves obtained by tea-rolling processing exhibit effects of controlling the storage of body fat. The results are shown in Table 9.

TABLE 9

| Sample | Weight of adipose tissues (g) |
| --- | --- |
| LETO - control diet | 38.2 |
| OLETF - control diet | 131.1 |
| OLETF - diet with powdery crude tea | 77.1 |
| OLETF - diet with powdery loquat leaves | 80.1 |
| OLETF - diet with powdery fermented tea leaves obtained by tea-rolling processing | 76.8 |

The cholesterol levels and neutral fat levels in the serum and liver of the OLETF rats in which the powdery crude tea or the powdery fermented tea leaves obtained by tea-rolling processing were fed were reduced, compared to those of the OLETF rats in which the control diet was fed. The results are shown in Table 10. It can be observed that the powdery crude tea and the powdery fermented tea leaves obtained by tea-rolling processing exhibit effects of reducing cholesterol and neutral fat.

TABLE 10

| Sample | Serum cholesterol (mg/dl) | Serum triglyceride (mg/dl) | Liver cholesterol (mg/g) | Liver triglyceride (mg/g) |
|---|---|---|---|---|
| LETO - control diet | 147 | 55.6 | 3.28 | 9.78 |
| OLETF - control diet | 253 | 234 | 5.98 | 49.5 |
| OLETF - diet with powdery crude tea | 183 | 127 | 3.43 | 16.9 |
| OLETF - diet with powdery loquat leaves | 238 | 237 | 4.90 | 34.1 |
| OLETF - diet with powdery fermented tea leaves obtained by tea-rolling processing | 177 | 139 | 3.08 | 12.6 |

From the results described above, it can be suggested that the composition having active components contained in the powdery fermented tea leaves obtained by tea-rolling processing exhibits effects of controlling the occurrence of diabetes, effects of controlling the storage of body fat, effects of reducing neutral fat and cholesterol in serum and the liver, and effects of reducing serum lipid peroxides.

In the following, the effects of Example 5 are described.

In Example 5 of the present invention, the effects described in the following can be obtained.

A composition having active components contained in the powdery fermented tea leaves obtained by tea-rolling processing with effectively unutilized tea material leaves and effectively unutilized loquat leaves exhibits effects of controlling the occurrence of diabetes, effects of controlling the storage of body fat, effects of reducing neutral fat and cholesterol in serum and the liver, and effects of reducing serum lipid peroxides. For this reason, the composition can be counted on for the treatment and prevention of lifestyle-related diseases and can contribute to the competitive powers of tea producers, loquat producers and dependent business.

Example 6

In Example 6, in order to study the functional properties of a composition having, as an active component, the extract contained in the fermented tea leaves obtained by tea-rolling processing of tea material leaves and loquat leaves which was produced in Example 1 (from Table 2, increased maltase inhibiting rate and increased sucrase inhibiting rate; blending ratio of loquat leaves of 10%, tea rolling period of 20 minutes, and fermentation period of 0 hours), animal experimentations with long-term administration were carried out.

Tea leaves are taken by drinking the powders thereof in some cases, but in general, by extracting these with hot water in many cases. Therefore, in order to study the functional properties of an extract with hot water of the fermented tea leaves obtained by tea-rolling processing of tea material leaves and loquat leaves which was produced in Example 1, animal experimentation with long-term administration was carried out.

The fermented tea leaves obtained by tea-rolling processing of tea material leaves and loquat leaves were extracted with hot water at 100° C., and the extract was freeze-dried. The freeze-dried extract was fed for 5 months to male rats at the age of 4 months in which type 2 diabetes naturally occurred, in the same manner as that of experiment 1. In addition, as comparative examples, an extract of crude tea with hot water at 100° C. or an extract of loquat leaves with hot water at 100° C. was fed to OLETF rats.

After 1, 2, 3, 4, and 5 months from starting administration of the test diet, the blood glucose levels were measured by means of a Medisafe Chip for monitoring blood glucose (Terumo Corporation, in Tokyo) by taking the blood from a tail vein after fasting for 6 hours. The change in the blood glucose levels of the rats in which the test diet was fed for 5 months is shown in FIG. 10.

Figure 10:
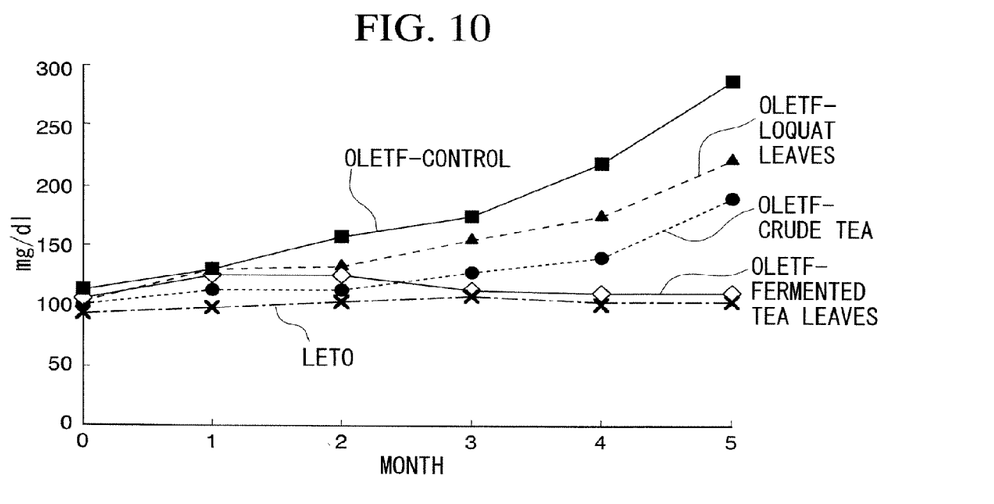
FIG. 10 is a graph showing changes in blood glucose levels in rats in which an extract of a fermented tea obtained by means of tea-rolling processing which was produced in Example 6, with hot water, was fed.

As shown in FIG. 10, the blood glucose level of the LETO rats in which the control diet was fed and diabetes did not occur was low over the rearing period, in the same manner as that of experiment 1. In contrast, the blood glucose level of the OLETF rats in which the control diet was fed and diabetes occurred was generally increased over time, and the occurrence of diabetes was observed. In addition, the blood glucose level of the OLETF rats in which the extract of crude tea with hot water or the extract of loquat leaves with hot water was fed tended to be increased over time, but was lower than that of the OLETF rats in which the control diet was fed. On the other hand, the blood glucose level of the OLETF rats in which the extract of the fermented tea leaves obtained by tea-rolling processing with hot water was fed was maintained at a low level over the rearing t period, and was a low level which was the same as that of the LETO rats. From the results described above, it is shown that the extract of the fermented tea leaves obtained by tea-rolling processing with hot water exhibits superior effects of controlling the elevation of blood glucose levels. Therefore, it can be seen that by subjecting tea material leaves and loquat leaves to tea-rolling processing and fermentation, components having new functional properties which are not included in the tea material leaves and loquat leaves might be produced.

The serum insulin levels of the OLETF rats in which the control diet, the extract of crude tea with hot water, or the extract of loquat leaves with hot water was fed were reduced after 5 months by the occurrence of diabetes. In contrast, the serum insulin level of the OLETF rats in which the extract with hot water of the fermented tea leaves obtained by tea-rolling processing was fed was increased to the same level as that of the LETO rats. The results are shown in Table 11. Therefore, it is shown that the extract with hot water of the fermented tea leaves obtained by tea-rolling processing can improve the reduction of insulin secretion caused by the occurrence of diabetes.

TABLE 11

| Sample | Insulin level (ng/ml) |
|---|---|
| LETO - control diet | 7.82 |
| OLETF - control diet | 3.10 |
| OLETF - diet with crude tea | 2.75 |
| OLETF - diet with loquat leaves | 2.55 |
| OLETF - diet with fermented tea leaves obtained by tea-rolling processing | 8.33 |

The weight of adipose tissues around testes and of the kidneys of the OLETF rats in which the extract with hot water of the fermented tea leaves obtained by tea-rolling processing was fed was lower than that of the OLETF rats in which the control diet, the extract with hot water of crude tea or the extract with hot water of loquat leaves was fed. The results are shown in Table 12. It was observed that the extract with hot water of the fermented tea leaves obtained by tea-rolling processing reduced body fat.

TABLE 12

| Sample | Weight of adipose tissues (g) |
|---|---|
| LETO - control diet | 37.0 |
| OLETF - control diet | 125.0 |
| OLETF - diet with crude tea | 115.8 |
| OLETF - diet with loquat leaves | 110.2 |
| OLETF - diet with fermented tea leaves obtained by tea-rolling processing | 94.7 |

The neutral fat levels in the serum and liver of the OLETF rats in which the control diet, the extract with hot water of crude tea, or the extract with hot water of loquat leaves was fed were significantly increased, compared to those of the LETO rats. In contrast, the extract with hot water of the fermented tea leaves obtained by tea-rolling processing effectively reduced the neutral fat levels in the serum and liver of the OLETF rats. The results are shown in Table 13. From these results, it can be suggested that the extract with hot water of the fermented tea leaves obtained by tea-rolling processing exhibits superior effects of reducing neutral fat.

TABLE 13

| Sample | Serum triglyceride (mg/dl) | Liver triglyceride (mg/g) |
|---|---|---|
| LETO - control diet | 70.1 | 12.4 |
| OLETF - control diet | 290 | 88.8 |
| OLETF - diet with crude tea | 278 | 105.5 |
| OLETF - diet with loquat leaves | 312 | 74.3 |
| OLETF - diet with fermented tea leaves obtained by tea-rolling processing | 170 | 43.9 |

From the results described above, it can be shown that the fermented tea leaves obtained by tea-rolling processing of tea material leaves and loquat leaves, in the form of a powder or an extract with hot water, effectively control the occurrence of diabetes. In addition, it was observed that the fermented tea leaves exhibited effects of controlling the storage of body fats. In addition, the fermented tea leaves controlled the neutral fat levels in serum and the liver. In particular, in the extract, with hot water, of the fermented tea leaves obtained by tea-rolling processing of the mixture of tea material leaves and loquat leaves, strong effects were observed, which could not be observed in the extract with hot water of crude tea or in the extract with hot water of loquat leaves. It is suggested that by mixing processing and tea-rolling processing, new components might be produced which are not included in tea material leaves or loquat leaves and exhibit effects of controlling the elevation of blood glucose levels, effects of preventing diabetes, effects of reducing body fat, and effects of reducing neutral fat in serum and the liver.

The fermented tea leaves obtained by tea-rolling processing of tea material leaves and loquat leaves were orally administered to male Sprague-Dawley rats at the age of 4 weeks at the dosage of 5000 mg/kg of body weight, and the rats were reared for 4 weeks under the conditions of a temperature of 22±1° C., humidity of 55±5%, and free feeding of the diet and water. As a result, mortality of rats was not observed, abnormal changes in body weight were not observed, and abnormalities in organs as autopsy results after completion of rearing were not observed. Therefore, the lethal dose ($LD_{50}$) of the fermented tea leaves with respect to rats may be estimated to be not less than 5000 mg/kg of body weight. It can be assessed that the fermented tea leaves have comparatively high safety.

From the results described above, a composition having, as an active component, the extract contained in the fermented tea leaves obtained by tea-rolling processing of tea material leaves and loquat leaves obtained in the present invention can be assessed to be sufficiently utilizable as healthy foods. In addition, the components included in the fermented tea leaves can be utilized as medicines.

In the following, the effects of Example 6 are described.

In Example 6 of the present invention, the effects described in the following can be obtained.

In a composition having, as an active component, the extract contained in the fermented tea leaves obtained by tea-rolling processing with employing unutilized tea material leaves and effectively unutilized loquat leaves by means of a new tea production technique with a specified mixing ratio, tea rolling period, and fermentation period, new components which were not included in tea material leaves or loquat leaves might be produced which exhibit effects of controlling the elevation of blood glucose levels, effects of preventing diabetes, effects of losing body weight, and effects of reducing neutral fat in serum and the liver. In addition, from the results of animal experimentation, safety thereof was assessed to be comparatively high. A composition having, as an active component, the extract contained in the fermented tea leaves obtained by tea-rolling processing of tea material leaves and loquat leaves can be sufficiently utilized as healthy foods, and at the same time, it can be expected that the components contained in the fermented tea leaves are utilized as medicines. For this reason, the composition can be expected for the treatment and prevention of lifestyle-related diseases and can contribute to the competitive powers of tea producers, loquat producers and dependent business.

As described above, the Examples of the present invention are described with reference to the drawings. It should be understood that the present invention is not limited to these examples, and modifications without departing from the scope of the present invention are also included in the present invention.

In addition, one or more materials selected from pear fruits, blueberries, leaves of *Camellia sasanqua*, egg apples, apple fruits, leaves of *Houttuynia cordata*, leaves of japonica, grapes, and ume apricot fruits may be added to the tea material leaves described in the aforementioned examples during the tea rolling step, the mixture is kneaded and fermented, and then the drying step is carried out at the same time as inspiring hot air.

INDUSTRIAL APPLICABILITY

The composition having, as an active component, the crude tea of the fermented tea leaves obtained by tea-rolling processing of tea material leaves and loquat leaves of the present invention, the refined tea leaves thereof, or the extract thereof, can be widely utilized as healthy foods, healthy beverages, and pharmaceutical compositions, which are useful in the treatment and prevention of lifestyle-related diseases.

What is claimed is:

1. A fermented tea obtained by tea-rolling processing of tea material leaves and loquat leaves characterized in that the fermented tea is produced by primary-drying tea material leaves by means of a primary tea rolling dryer (primary drying step) to reduce a moisture content while stirring with hot air; subsequently, providing the primary-dried tea material leaves in a tea roller (tea rolling step); adding loquat leaves during the tea rolling step in order to knead loquat leaves together with the tea material leaves into a mixture; fermenting the mixture; and drying the kneaded tea material leaves and loquat leaves to carry out a drying step at the same time as stopping the fermentation by inspiring hot air.

2. The fermented tea obtained by tea-rolling processing of tea material leaves and loquat leaves according to claim 1, wherein in said tea rolling step, the loquat leaves are added in an amount of 10 to 25% by weight based on the tea material leaves, and kneaded together with the tea material leaves for 15 to 25 minutes, followed by carrying out the fermentation step within 4 hours and the drying step at the same time as stopping the fermentation by inspiring hot air.

3. The fermented tea obtained by tea-rolling processing of tea material leaves and loquat leaves according to claim 1, wherein in said tea rolling step, the loquat leaves are added in an amount of 9 to 11% by weight based on the tea material leaves, and kneaded together with the tea material leaves for 15 to 25 minutes, followed by carrying out the fermentation step within 1 hour and the drying step at the same time as stopping the fermentation by inspiring hot air.

4. A composition comprising, as an active component, an extract contained in a crude tea or refined tea based on a fermented tea obtained by tea-rolling processing of tea material leaves and loquat leaves characterized in that the fermented tea is produced by primary-drying tea material leaves by means of a primary tea rolling dryer (primary drying step) to reduce a moisture content while stirring with hot air; subsequently, providing the primary-dried tea material leaves in a tea roller (tea rolling step); adding loquat leaves during the tea rolling step in order to knead loquat leaves together with the tea material leaves into a mixture; fermenting the mixture; and drying the kneaded tea material leaves and loquat leaves to carry out a drying step at the same time as stopping fermentation by inspiring hot air.

5. The composition according to claim 4, wherein the composition is employed as a healthy food, a healthy beverage, or a medicinal product in an effective amount for controlling an elevation of blood glucose levels.

6. The composition according to claim 4, wherein the composition is employed as a healthy food, a healthy beverage, or a medicinal product, for use in controlling an occurrence of diabetes or ameliorating diabetes.

7. The composition according to claim 4, wherein the composition is employed as a healthy food, a healthy beverage, or a medicinal product, for use in controlling or decreasing body fat accumulation.

8. The composition according to claim 4, wherein the composition is employed as a healthy food, a healthy beverage, or a medicinal product, for use in reducing cholesterol.

9. The composition according to claim 4, wherein the composition is employed as a healthy food, a healthy beverage, or a medicinal product, for use in decreasing neutral fat.

10. The composition according to claim 4, wherein the composition is employed as a healthy food, a healthy beverage, or a medicinal product, for use in reducing serum lipid peroxides.

* * * * *